United States Patent [19]

Anderson et al.

[11] Patent Number: 5,378,991
[45] Date of Patent: Jan. 3, 1995

[54] DETECTING DEGRADATION OF NON-CONDUCTIVE INERT WALL LAYERS IN FLUID CONTAINERS

[76] Inventors: Thomas F. Anderson, 535 Oak Dr., Lake Jackson, Tex. 77566; Otto H. Fenner, 650 Hollywood Pl., Webster Groves, Mo. 63119; Richard D. Fenner, 7303 Springside, Houston, Tex. 77040

[21] Appl. No.: 889,284

[22] Filed: May 27, 1992
(Under 37 CFR 1.47)

[51] Int. Cl.⁶ ............... G01N 27/00; G01R 31/12
[52] U.S. Cl. .................... 324/557; 324/450; 324/512
[58] Field of Search ........... 324/439, 450, 525, 512, 324/536, 551, 557, 693, 722

[56] References Cited

U.S. PATENT DOCUMENTS

| | | | |
|---|---|---|---|
| 3,252,155 | 5/1966 | Surtees et al. | 324/557 X |
| 3,555,414 | 1/1971 | Deichelmann | 324/557 |
| 3,831,085 | 8/1974 | Kratavil | 324/557 |
| 3,858,114 | 12/1974 | Voellmin et al. | 324/557 |
| 3,863,146 | 1/1975 | Ehret | 324/557 |
| 3,965,415 | 6/1976 | Ehret | 324/557 |
| 4,110,739 | 8/1978 | Kidd | 340/605 |
| 4,161,689 | 7/1979 | Schlosberg et al. | 324/557 |
| 4,188,267 | 2/1980 | Seger et al. | 324/551 X |
| 4,523,141 | 6/1985 | Thomas et al. | 324/54 |
| 4,546,310 | 10/1985 | Chatanier et al. | 324/525 |
| 4,689,552 | 8/1987 | Fujii et al. | 324/512 |
| 4,771,246 | 9/1988 | Boryta et al. | 324/559 |
| 4,844,287 | 7/1989 | Long | 220/429 |
| 4,922,232 | 5/1990 | Bosich | 340/605 |
| 4,985,682 | 1/1991 | Boryta | 324/557 |
| 4,989,447 | 2/1991 | Gelin | 73/49.2 |
| 4,993,581 | 2/1991 | Mitchell | 220/453 |
| 5,119,032 | 6/1992 | Grimwood | 324/557 |
| 5,191,785 | 3/1993 | Kidd et al. | 73/49.2 |
| 5,214,387 | 5/1993 | Fenner | 324/557 |

OTHER PUBLICATIONS

"Conductivity Probe Guards Against FRP Degradation", Chemical Engineering, Jul. 1991, p. 163.
"Permtron TM Monitoring System", Fenner & Associates, Inc. Brochure, Jul. 1991, pp. 1–6.
Chandler et al., "Synthetic Veil–Why and How To Use It (In Corrosion Resistant Equipment)," The Society of the Plastics Industry, Inc., 39th Annual Conference, Jan., 1984, pp. 1–9.

*Primary Examiner*—Kenneth A. Wieder
*Assistant Examiner*—Glenn W. Brown

[57] ABSTRACT

A fluid contained in a vessel of multi-layer wall construction can intrude, because of damage or wear, through the inner containment layer and signal a problem with the life expectancy or safety of the vessel. By providing vessel walls having alternating layers of conductive material and non-conductive material, and by providing electrical connections for effecting circuitry to an instrument for measuring electrical properties across the inner containment layer, then intrusion of fluid into or through the inner wall can be detected by the instrument. For a conductive fluid, the inner layer of the vessel wall should be non-conductive and the layer covering that inner layer should be conductive. For a non-conductive fluid, the inner layer of the vessel wall should be conductive, and the layer covering that inner layer should be a non-conductive which is covered by another conductive layer. In many instances, it is preferred that the electrical property measured is the change in resistance, on the megohm scale. Other electrical measurements, such as amperage, dielectric constants, power factor, loss factor, or capacitance can be made.

28 Claims, 7 Drawing Sheets

DETECTING DEGRADATION OF NON-CONDUCTIVE INERT WALL LAYERS IN FLUID CONTAINERS

CROSS-REFERENCE TO RELATED APPLICATION

This is related, in part, to subject matter contained in pending application Ser. No. 07/319,615 filed Mar. 6, 1989, now U.S. Pat. No. 5,214,387.

FIELD OF THE INVENTION

Measuring electrical properties of substantially inert, non-conductive walls or liners of multi-layered fluid containers.

BACKGROUND OF THE INVENTION

For several decades there has been an increasing usage of a variety of plastics, such as fiberglass reinforced plastics (also called FRP), as materials of choice for storing and/or transporting a wide variety of fluids, such as water, fuels, chemicals, compressed gases, waste products, brine, fumed products, and the like. The choice of plastic usually depends, at least in part, on the amount of chemical and/or solvent inertness required and also on the abrasiveness and temperature of the product being stored or transported. The containers can range from relatively small sizes, such as drums, to very large sizes, such as storage tanks, rail tank cars or shipping barges, or very elongated containers, such as pipes or ducts or other conduits.

At times the plastic, including reinforced or laminated plastic, comprises essentially the entire wall structure of the container, and sometimes a container is merely lined with plastic. In any event, whether the plastic comprises the entire container or only serves as a liner in a container made of some other material (usually metal or a composite material) the rate of wear, damage, or deterioration may require testing or monitoring, especially if a leakage of fluid stored or carried in the container might create an unacceptable detriment to flora and/or fauna, or constitute a violation of the law. Such problems can be appreciably avoided if excessive wear of the container wall or damage to the container wall is detected soon enough by monitoring electrical changes in the wall due to permeation or intrusion of the contained fluid into the container wall. It has been determined that virtually any fluid contained in a non-conductive, inert container, while often being a fluid having very poor electrical conductivity, can create a detectable change in the electrical properties of the non-conductive inert container by intrusion or permeation of the fluid into the non-conductive, inert container wall at points of imperfect construction, damage or degradation if means can be provided for monitoring the electrical properties using non-destructive testing. Fluids which are essentially electrically non-conductive, but which may intrude into the wall in which they are contained, also pose a problem for which a remedy is needed.

As disclosed in Chemical Engineering, page 464, Jul. 1991, a means has been developed for detecting changes in the electrical properties of a container wall comprising FRP which the gradual intrusion of a stored aggressive substance into the wall can be monitored. The means involves, as the monitoring device, a set of probes embedded at various depths in predetermined areas in the FRP wall to operate in circuitry with a "wet" probe which penetrates through the wall to be in contact with the fluid within the container. The embedded probes and the wet probe are each connected to an electrical receptacle mounted on the exterior of the wall with a means for connection to a microammeter. In a related brochure it is suggested that in areas of secondary joints, such as incoming pipes, a graphite fiber mat that completely encompasses the joint can be substituted for a probe. The above-described means and method, which monitors a relatively small area in which the embedded probes and their cooperating wet probe are located, may fail to give an early warning of a damaged or badly eroded container wall at a location which is not near enough to the probes to be effectively indicated by the microammeter.

The use of a carbon or graphite veil behind a non-conductive thermoplastic liner for a thermoset fiberglass structural tank has been used to allow spark testing of the thermoplastic liner to assure there are no micro holes or cracks in the liner that would allow a corrosive material to get behind the liner and into the thermoset fiberglass structural part of the tank. A spark generator is used for finding tiny holes or cracks that are too small to be seen by the naked eye; any such imperfections in the thermoplastic liner which reach the carbon or graphite veil will provide a path to "ground" which is evidenced by a visibly strong spark from the spark generator to the hole or crack. This type of test does not require that an electrical conductor wire be connected to the conductive layer and protrude to a location outside the wall of the tank for connection to an electrical measuring instrument. Also, this type of testing is used as a quality test for new vessels, where the spark generator is normally swept across the inner surface of the container before being placed in service. The spark generator can also be used when the container has been emptied for cleaning or inspection and the inner surface of the container re-tested. The spark generator is not used to test the inside surface of containers while the containers are filled with fluid.

It is an object of this invention to provide a means and method which can be used in monitoring the electrical properties across a liner, essentially of an entire container, or at least a relatively large portion of a large container, and not rely simply on many probes which monitor only a relatively small area per probe.

It is also an object of this invention to employ a "wet" probe which can be removed when no measurements are being made, or if mounted therein can be easily replaced if damaged, without being permanently mounted as projections through the inner surface of the container wall per se, whereby there can form a crevice around the probe which, itself, can promote degradation of the wall due to intrusion of the stored fluid into the crevice around the projecting probe, especially where changes in temperature coupled with different coefficients of expansion can cause leaks.

It has now been discovered that an electrically insulating material (i.e. a non-conductive material) used as a substantially inert material to contain a fluid that has at least some electrical conductivity, can have its fluid-containment ability monitored by measuring the electrical properties across the non-conductive material between the fluid in the container and an electrical conductor co-extensively in contact with and surrounding the electrically insulating, substantially inert material. Penetration or intrusion of the electrically conductive liquid into or through the liner, will result in a loss in the electrical insulation properties; the loss can be detected and/or monitored and the data gathered can be used to predict or determine when the inertness or integrity of the containment layer will no longer be capable of satisfactorily containing the liquid.

Ways and means have now been developed for detecting and/or monitoring damage, degradation or deterioration of any part of a containment wall of a fluid container (e.g., tank, barge, pipe, duct, pump, flume, etc.) wherein there is an electrically conductive fluid contained within an electrically-insulating material such as plastic, rubber, ceramic, refractory and the like. In the present invention, described more fully below, there is provided as a part of the containment wall, at least one electrically-conductive veil or layer which is separated from the contained fluid by the chemically-resistant electrically-insulating material, the said conductive veil or layer being firmly attached co-extensively to the electrically-insulating containment layer of the wall. The conductive veil or layer is provided with attached means for connecting at least one conductor wire to an instrument for measuring electrical properties, whereby intrusion of the fluid into the containment wall can be detected and/or monitored.

As used in this disclosure, the term "inert layer" means that the containment layer of the multi-layer wall is essentially chemically inert to, or is not readily dissolved or otherwise substantially attacked by, the fluid in the containment portion of the fluid container. The terms "non-conductive" and "conductive" refer to electrical properties unless stated otherwise, it being understood by practitioners of these relevant arts that if the conductivity is low enough (essentially nil for all practical purposes) then it may be non-conductive enough to function as an electrical insulator depending on the relative level of electrical power involved. The terms "conductor", "conductive wire" and "wire" are used in describing a means for electrically connecting portions of the containers to instruments or to other conductors to provide circuitry for measuring electrical properties. Generally a metal wire is used, though conductive ribbons, rods, webs, meshes, graphite tows or strips or other configurations are within the purview of the present inventive concept.

When using instruments to measure electrical properties, practitioners will be expected to employ the usual procedure of impressing a DC voltage through appropriate circuitry and "zeroing" the instrument to provide a reference point against which to compare subsequent measurements of the circuit to be tested. The voltage can be from less than 1 volt to about 2,500 volts or more, depending on which electrical property one wishes to measure. About 500 to about 1000 volts is generally suitable for measuring megohms in the present invention when testing containers which contain non-flammable fluids, though different voltages may be found to be better in measuring other electrical properties such as amperage, capacitance, power factor, dielectric constant, loss factor, or scanning for voids using spark generators using voltages up to about 50,000. When measuring containers that contain flammable fluids, it is recommended that very low voltages be used, especially voltages of less than 1 volt, in order to avoid creation of a spark where flammable vapors could be ignited.

SUMMARY OF THE INVENTION

In the devices and methods of the present invention, accommodation is made, on the one hand, for fluids which are good conductors of electricity, or have at least some detectable electrical conductivity, and on the other hand for fluids which are essentially electrically non-conductive.

The basic features of the multi-layered fluid containers of the present invention comprise:

at least one conductive layer as a wall component of the container, said layer being essentially co-extensive with, and intimately covering, the fluid-containment inner layer portion of the container, an essentially inert, non-conductive inner layer between and electrically insulating each of the at least one conductive layer(s) from the fluid-containment portion of the container, at least one electrical conductor extending from each of the at least one conductive layer(s) said conductor being connectable to an instrument for measuring electrical properties, and at least one fluid-wettable probe comprised of conductive material which is connectable by a conductor wire to the said instrument, and positionable to be in contact with fluid in the fluid-containment portion of the container.

A method of making electrical measurements across an essentially inert, essentially non-conductive containment layer of a fluid container, when it contains fluid and circuitry between the conductive layer and fluid and instrument have been established, said method comprising:

measuring the electrical properties of the non-conductive layer of the wall by impressing a DC voltage through cooperating conductors which are separated by the non-conductive layer of the wall, thus establishing an initial reference point, and thereafter repeating, or continuing, the process as desired to monitor the degradation rate of, or intrusion of the fluid into, the non-conductive layer as indicated by changes in reference to the initial reference point.

In applying the present invention to vessels which are used for holding or conveying non-conductive fluids, the positioning of the conductive and non-conductive layers of the vessel are different. In this case a first conductive layer comprises the inside fluid-containment layer (even though it may have a thin surface coating of resin) and its enveloping non-conductive layer (e.g. FRP) is surrounded by a second conductive layer. Conductors attached to the first conductive layer extend through the non-conductive layer and through the second conductive layer without being in electrical contact with the second conductive layer for connection to instrument wiring. Conductors attached to the second conductive layer are connectable to instrument wiring at the opposing pole from the first conductive layer. The conductive layers can be prepared, for example, by using in the laminate structure graphite veils which are impregnated with resin before the resin is cured to a solid. The conductive layers can be metal. One layer can comprise metal and one can comprise a conductive resin.

In a related embodiment, which relies on having at least one conductive inner layer co-extensively embedded within the wall of an FRP container, imperfections such as breaks, damage, or void spaces (tiny holes, cracks, and the like) in the FRP can be detected by using a spark generator which uses high voltage (usually within the range of 10,000 to 50,000 volts) to sweep the wall of the container. Imperfections in the FRP can provide paths of least resistance through an insulating layer for sparks to reach the embedded conductive layer; the sparks are easily visible to the human eye, being evidenced by the whiteness and intensity of the spark which is formed in the corona emitted between the spark generator probe and the surface being tested. A spark generator can be used not only for an initial quality testing of a newly made container, but can also be used to pinpoint areas of concern which are detected by measuring changes in electrical properties across the inner layer of a container that has been in service.

It is within the purview of the present inventive concept that the electrical readings be used in conjunction with computer programs to regulate the frequency or duration of tests, and even to signal a corrective response upon detecting a pre-determined set of conditions.

BRIEF DESCRIPTION OF DRAWINGS

FIG. 1 is used in relating a container comprising a fluid-containment portion within an inert, non-conductive material, with a conductive layer co-extensively enveloping and co-extensively in contact with, the non-conductive material, and separated from the fluid by the fluid-containment layer. By use of conductors in circuitry with an instrument for measuring electrical properties across the non-conductive layer, intrusion of fluid into the containment wall is detected and/or monitored.

FIG. 2, is used in relating a container comprising a fluid-containment portion in an inert, non-conductive material which is co-extensively enveloped in a conductive material.

FIG. 3, is used in relating an elongate container comprising a fluid-containment portion within an inert, non-conductive layer which is co-extensively enveloped by a conductive layer FIG. 4, is used in relating an elongate container comprising a fluid-containment portion within an inert, non-conductive layer which is co-extensively enveloped by a conductive layer.

FIG. 5 is used in relating a container comprising a fluid-containment portion within an inert, non-conductive layer which is co-extensively enveloped by a conductive layer.

FIG. 6 is used in relating a tall container comprising a fluid-containment portion within an inert, non-conductive layer which is almost completely co-extensively enveloped by a conductive layer which is intentionally prepared so as to have some discontinuity in the conductive layer.

FIG. 7 is used in relating an elongated container comprising a fluid-containment portion within an inert non-conductive layer which is almost completely co-extensively enveloped by a conductive layer which is intentionally prepared so as to have some discontinuity in the conductive layer.

FIG. 8 is used in relating a container which comprises a fluid-containment portion within an inert, non-conductive layer which is surrounded, in turn, by a conductive layer, another non-conductive layer, another conductive layer, and an outer layer.

DETAILED DESCRIPTIONS INCLUDING BEST MODE CONTEMPLATED BY THE INVENTORS

Figure 1:
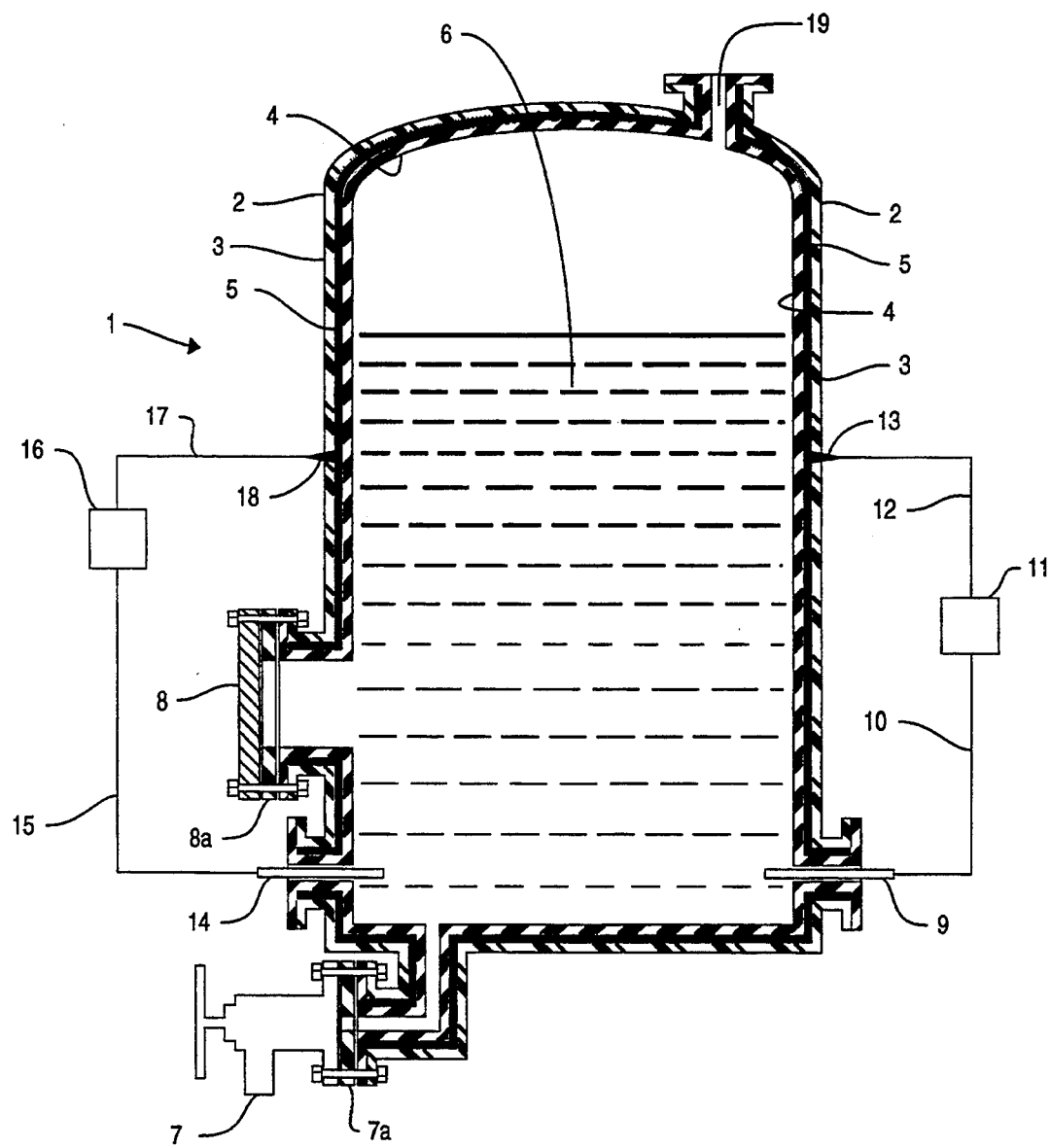
FIGS. 1 to 8 are cross-sectional views of vessels, none of which are drawn to any particular scale, that are provided as visual aids for relating certain basic features of a variety of embodiments of the present invention, including the use of a single layer of conductive material and the use of more than one layer of conductive material.

Certain principles involved in this invention are: (1) that inert (or substantially inert) materials that are electrical insulating materials show a loss in electrical insulation resistance, over extended periods of time, when they are penetrated and/or degraded by the corrosive environments to which they are exposed; and (2) if the corrosive environment is electrically conductive and a conductive layer completely surrounds the container or an inner liner of the container, electrical measurements can be made while the equipment is in service to determine if the electrical insulation resistance is decreasing due to changes brought about by degradation or intrusion of the fluid into the container wall. This gives an indication of changes, if any, in the container.

As used in this disclosure, the expression FRP (meaning fiberglass reinforced plastic) is representative of one main type of container construction material that is often used in industry, but the present invention is not limited to only those which are reinforced by fiberglass, nor is it limited to any particular plastic. Other fibrous material may be used in some circumstances where temperature, cost, availability, structural strength, chemical resistance, and other factors may suggest or require that other fibers, fillers or reinforcement be used. In some cases, where a layer of plastic is only needed to provide a measure of inertness or corrosion resistance, and is not necessarily depended on for the structural strength of the container (such as plastic-lined pipe or plastic-lined vessels), reinforcement may not be needed.

The inert or corrosion-resistant, essentially non-conductive inner wall of the container may be a ceramic or other refractory material or may be a plastic (in some cases often called resins). Often used is an epoxy resin, urethane resin, polyester, or vinyl ester resin, but can also be a polymer of an olefin, a substituted olefin (such as a haloolefin, chlorofluoroolefin and the like), a polyvinyl compound (such as polyvinyl chloride, polyvinlidene chloride, polyvinylidene fluoride), a polydiolefin (such as used in making rubber products and prepared using polymers comprised of butadiene, styrene, isoprene, or chloroprene), polycarbonate, polyacrylates, polymethacrylates, polyethyleneterephalate, and the like. Any storage or carrier containers for fluids which have fluid contained within a wall of inert or corrosion resistant materials which are essentially non-conductors of electricity, and which may be subject to intrusion of fluids contained therein, may benefit by application of the present invention to monitor the degradation of, or intrusion into, the wall by the stored fluid.

In some embodiments a conductive layer (e.g. a film, web or mesh) is used as an inner layer encapsulated in a multi-layer plastic laminate, and is preferably a conductive carbon or graphite or metal. The encapsulated conductive material requires considerably more conductivity than the plastic which surrounds it. Preferably the conductive layer is a mesh or other thin layer which is porous enough for the plastic layers on each side of it to form bonding sites through the pores to make a strong laminate. Thin sheets or "veils" of carbonized woven or non-woven organic materials are commerically available which have very small holes and through which plastics or resins on each side of the veil can form linking bonds, thus encapsulating the conductive carbon material. Another embodiment of conductive layer is a plastic mesh or porous mat which is impregnated with a conductive resin, such as a resin filled with conductive carbon, metal particles, or other conductive particles or substances.

Persons who are skilled in the art of making FRP vessels, or plastic-lined vessels should be able to use their skills in adding one or more conductive layers into the plies of material used in the industry in "laying-up" or constructing a laminated structure or in lining existing structures with a conductive layer covered by an inert, non-conductive layer or in lining a non-conductive layer with a conductive layer. Preparation of a container having an inner encapsulated conductive layer in accordance with the present invention may be carried out substantially as is normally done in preparing laminates, except that the inner conductive layer is used along with any layers of fiberglass or other reinforcement which may be used in the laminate structure, providing in addition a conductor (e.g. a wire) which is connected to the inner encapsulated conductive layer and which protrudes through the wall of the container for connection to an instrument for measuring electrical properties.

Adding an electrical conductor wire, strap, or mesh to an existing structure which has a conductive layer embedded as an inner layer within a multi-layer wall can be done by carefully drilling or grinding a hole through the outer layer, being careful not to destroy any significant amount of the conductive layer, and soldering or otherwise electrically bonding the conductor wire, strands, strap or mesh to the conductive layer. For example, electrically bonding a conductor to a conductive layer can be done using a silver amalgam. The hole can then be filled with material that will form a suitable patch, taking care to keep the connection intact and permitting the wire, strap or mesh to extend outside the patch.

Referring further to the figures, FIG. 1 is presented as a visual aid in relating embodiments of the present invention. A plastic container, indicated generally by the number 1, comprises a wall 2 which has an outside layer 3 and an inside layer 4. Encapsulated between layers 3 and 4, and essentially co-extensive with wall 2, there is depicted a layer of conductive material 5 (shown as a thick black line for easier understanding of the figure), which has a first conductor wire 12 connected to it at site 13 with the other end of wire 12 connected to one pole of an instrument 11 suitable for measuring electrical properties. A second conductor wire 10 is connected to the other pole of the instrument and with a probe end 9 protruding into fluid 6 in the container, a read-out can be obtained on the instrument. Also shown is a conductor wire 17 attached at one end to conductor 5 and at the other end to instrument 16; with a conductor wire 15 connected to probe 14 protruding into fluid 6 and the other end attached to instrument 16, a read-out can be obtained. It is not necessary that circuitry for more than one electrical measuring instrument be employed, but it can provide verification at a different part of the container. Probes 9 and 14 can be positioned in ports (such as those referred in industry as "flanged nozzles") in substantially the same manner in which other ancillary devices, such as thermocouples, are commonly positioned and sealed to prevent leakage around the device. Also shown is a port 19 at the top for loading fluid into the container; one can insert a probe into the fluid through the loading port for providing a circuitry to a measuring device instead of, or in addition to, using probe 9 or 14. At the bottom of the container is shown a valve 7 with gasket 7a for draining the container, which is customary for many such containers. At one side of the container there is shown a closure plate 8 and its cooperating gasket 8a covering an access port which can be used for cleaning or inspecting the container. If the closure plate is made of conductive material, and the inside face is exposed to the fluid as shown in the figure by the fact that the gasket does not cover the entire closure plate, one may attach a probe to it for completing a test circuitry with an instrument 11 or 16 in cooperation with probe 13 or 18 for measuring an electric property of inside layer 4 instead of, or in addition to, probes 9 and 14. If one wishes, and if valve 7 is made of conductive material which is in contact with fluid 6 because of the central opening in gasket 7a, then a conductor wire can be attached to the valve for use as a probe instead of, or in addition to, probe 14 or 9. There can be more or fewer connection points with the conductor and/or with the fluid. The plastic may be an FRP or other non-conducting material, and can be different on each side of the conducting layer. The conductive layer can be any conductive material such as carbon veil, conductive graphite sheet, or metal mesh, taking into account that having at least some porosity is important in having penetration of the plastic into the conductive layer to provide integrity in the laminate structure.

Figure 2:
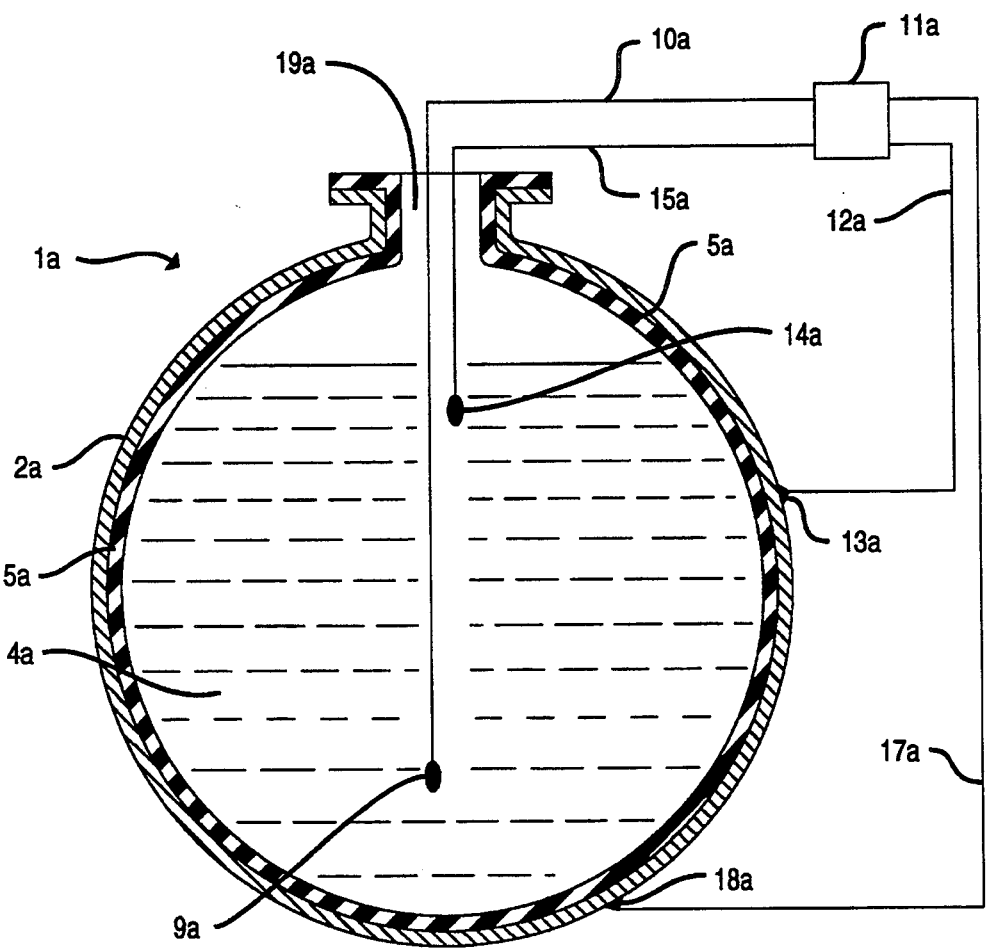

FIG. 2 is presented as a visual aid in further relating embodiments of the invention. A vessel, generally identified as 1a, comprises outer conductive layer 2a lined with inert, non-conductive layer 5a. Attached to conductive layer 2a at point 18a is conductive wire 17a which is connectable to instrument 11a for providing circuitry through conductor 10a to probe 9a lowered into fluid 4a through port 19a. Also attached to conductive layer 2a at point 13a is wire 12a which is connectable to instrument 11a for providing circuitry with conductor wire 15a to probe 14a. The instrument is used for measuring electrical properties across non-conductive layer 5a at intervals, or continuously, to detect intrusion of fluid into non-conductive layer 5a. It is optional to have more than one circuitry, but such redundancy is often used as insurance against reliance on a malfunctioning single circuit.

Figure 3:
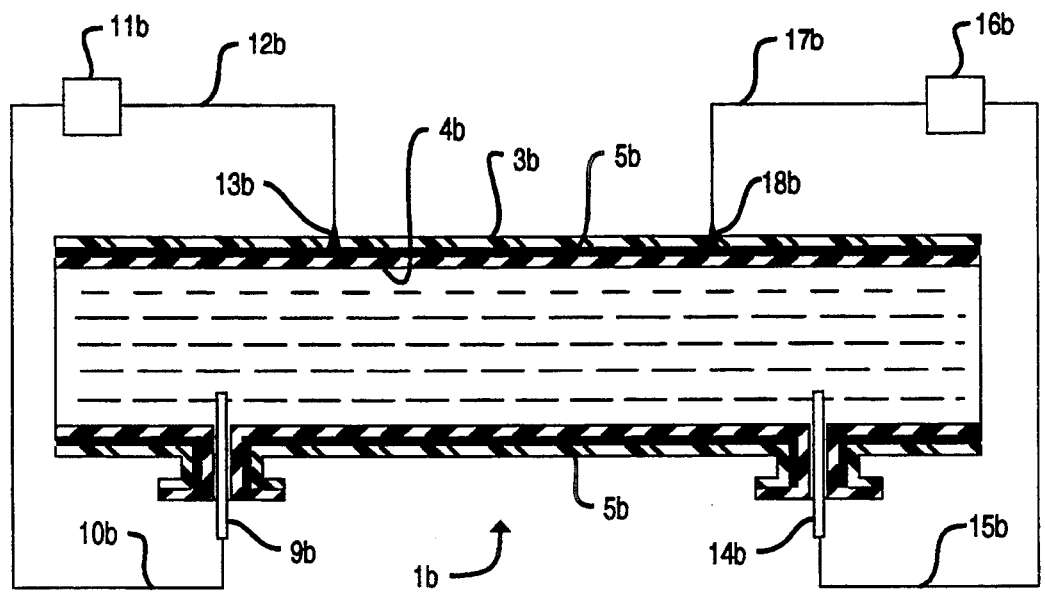

FIG. 3 is also presented as a visual aid in further relating embodiments of the invention. An elongate structure, shown generally as 1b, represents a portion of a pipe or duct structure having an outer layer 3b, an inside non-conducting layer 4b, and a middle conductive layer 5b (shown as a broad black line). Probe 9b is inserted into fluid inside the structure through any suitable port and is connectable to instrument 11b by wire 10b, with circuitry to conductive layer 5b being completed by wire 12b at connection point 13b. In similar manner probe 14b is connectable by wire 15b to instrument 16b which is connectable by wire 17b to connection point 18b on conductive layer 5b.

Figure 4:
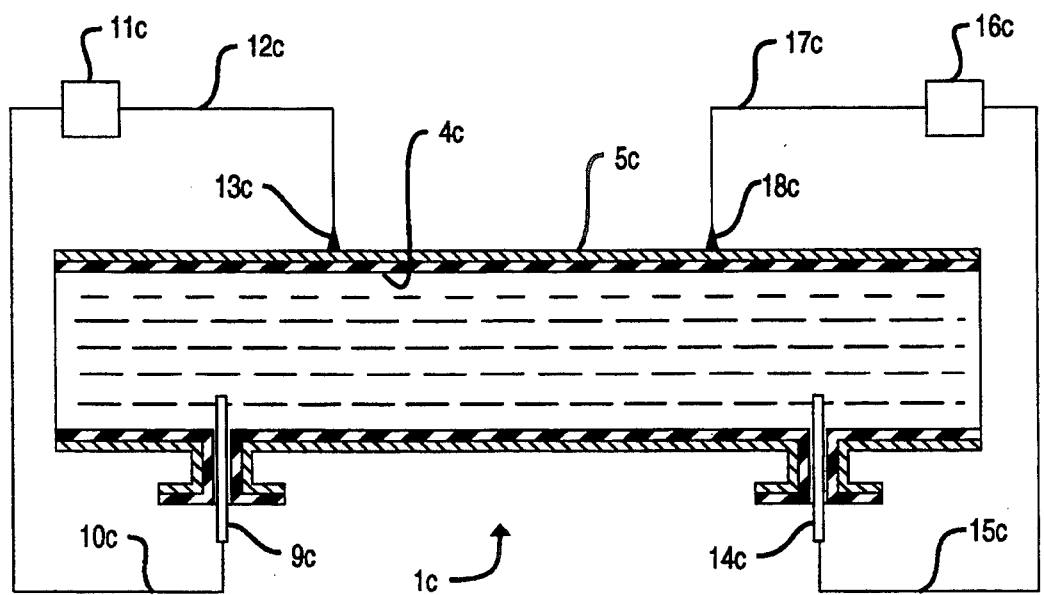

FIG. 4 is also presented as a visual aid in further relating embodiments of the invention. An elongate structure, shown generally as 1c, represents a portion of a pipe or duct structure having an outer conductive layer 5c, and a non-conducting layer 4c. Probe 9c is inserted into fluid inside the structure through any suitable port and is connectable to instrument 11c by wire 10c, with circuitry to conductive layer 5c at connection point 13c being completed by wire 12c. In similar manner probe 14c is connectable by wire 15c to instrument 16c which is connectable by wire 17c to connection point 18c on conductive layer 5c.

Figure 5:
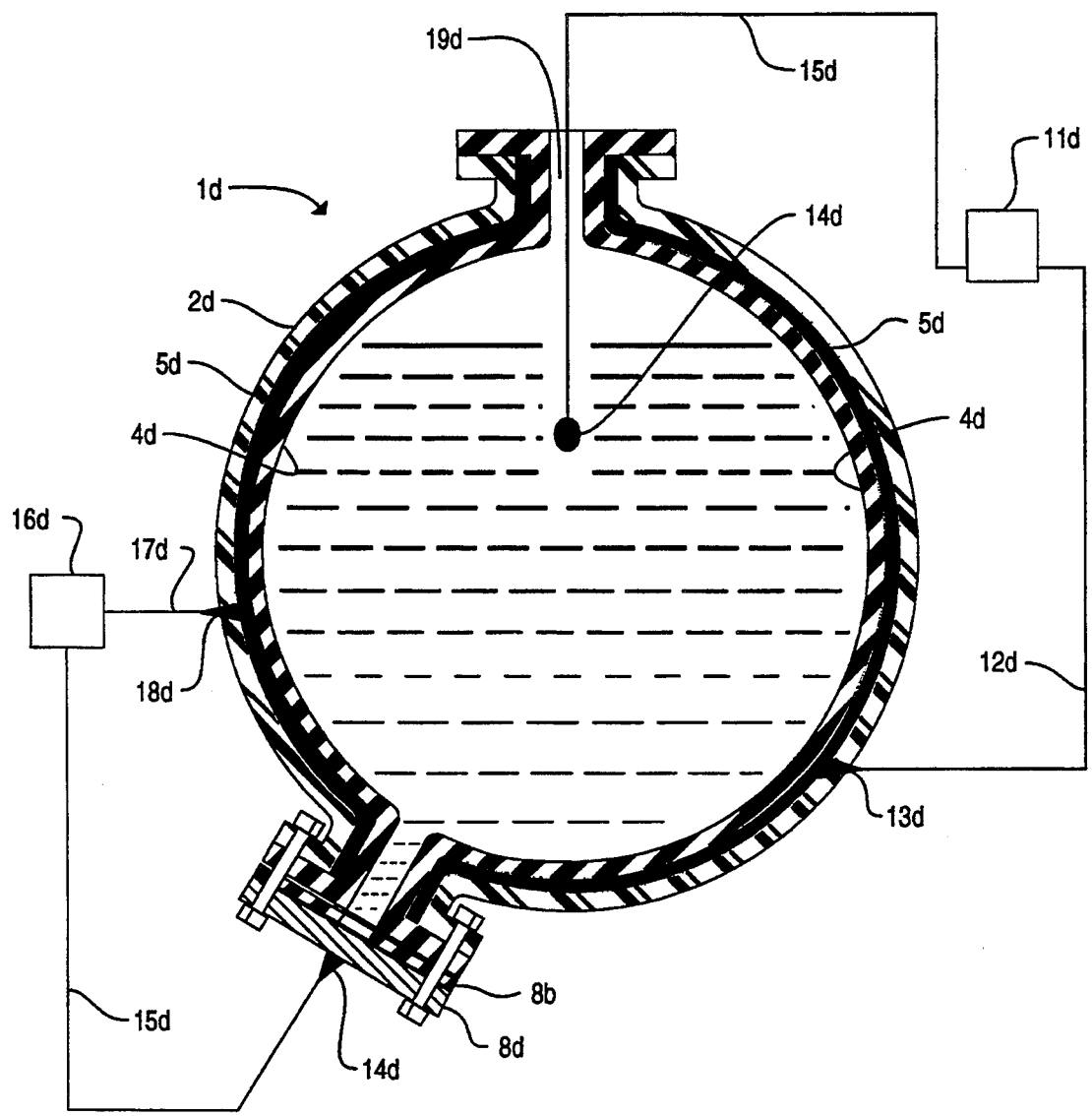

FIG. 5 is presented as a visual aid in relating embodiments of the present invention. A plastic container, indicated generally by the number 1d, comprises a wall having a non-conductive layer 2d and an non-conductive layer 4d. Encapsulated between layers 2d and 4d, and essentially co-extensive therewith, there is depicted a layer of conductive material 5d (shown as a thick black line for easier understanding of the figure), which has a first conductor wire 12d connected to it at point 13d with the other end of wire 12d connectable to an instrument 11d suitable for measuring electrical properties. Another conductor wire 15d is connectable to the other pole of the instrument 11d and with a probe end 14d protruding through port 19d into fluid 6 in the container, a readout can be obtained on the instrument. Alternately a conductor wire 17d is attached at one end to conductive layer 5d at point 18d and at the other end to instrument 16d; with conductor wire 15d connected to probe 14d affixed to metal flange cover 8d which is in contact with fluid 6 inside the vessel and the other end attached to instrument 16d, a read-out can be obtained. Taking the measurement through the use of the metal flange cover at the bottom can be convenient if there is reason not to open the port at the top of the vessel. It is not necessary that circuitry for more than one electrical measuring instrument be employed, but it can provide verification at a different part of the container. There can be more or fewer connection points with the conductor and/or with the fluid. The plastic may be an FRP or other non-conducting material, and can be different on each side of the conducting layer. The conductive layer can be any conductive material such as carbon veil, conductive graphite sheet, or metal mesh, taking into account that having at least some porosity is important in having penetration of the plastic through the conductive layer to provide integrity in the laminate structure.

Figure 6:
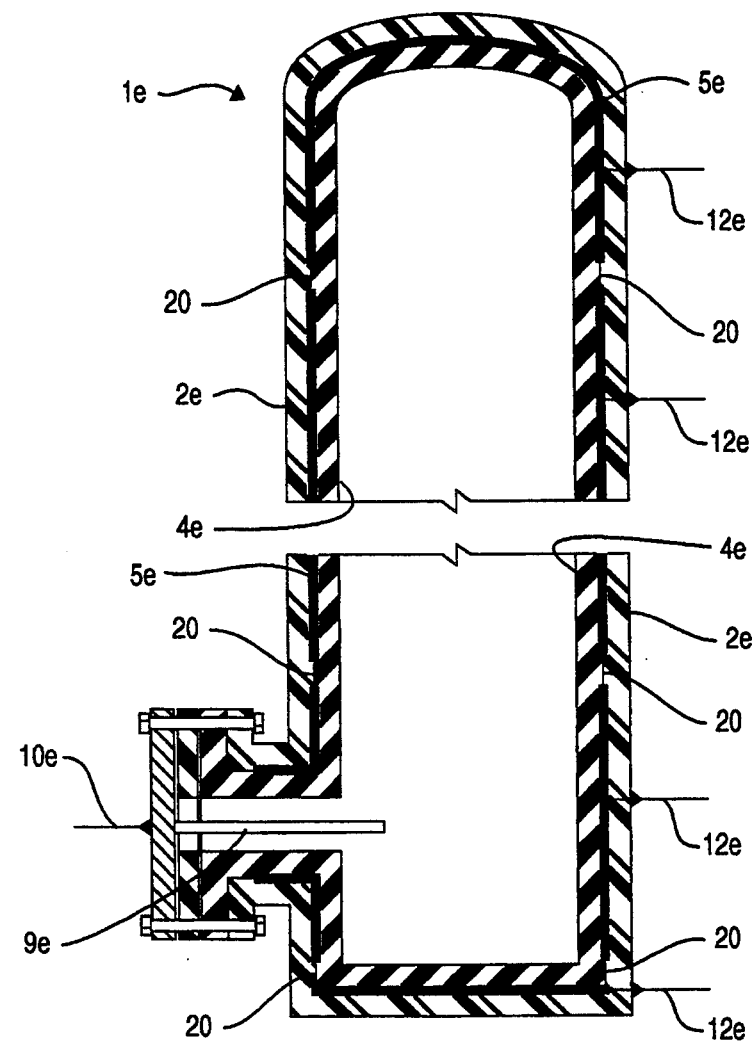

FIG. 6 is used for relating other embodiments of the invention. There is depicted, as a visual aid, a tower of indeterminate height, shown with central portion excised, identified generally as 1e, having an outer layer 2e, and inner layer 4e, a conductive layer 5e, electrical connections 12e to layer 5e shown along one side, with probe 9e reaching into the fluid containment section and connectable from point 10e on the metal flange cover to an instrument (as shown in other figures) for measuring electrical properties when in circuitry with any of the connections 12e. In order to separately test several large portions of layer 5e, intentional discontinuities are provided as indicated at points 20; in this manner, one can more closely pinpoint potential problem spots in a tall tower or large vessel, as detected by variances in the electrical measurements.

Figure 7:
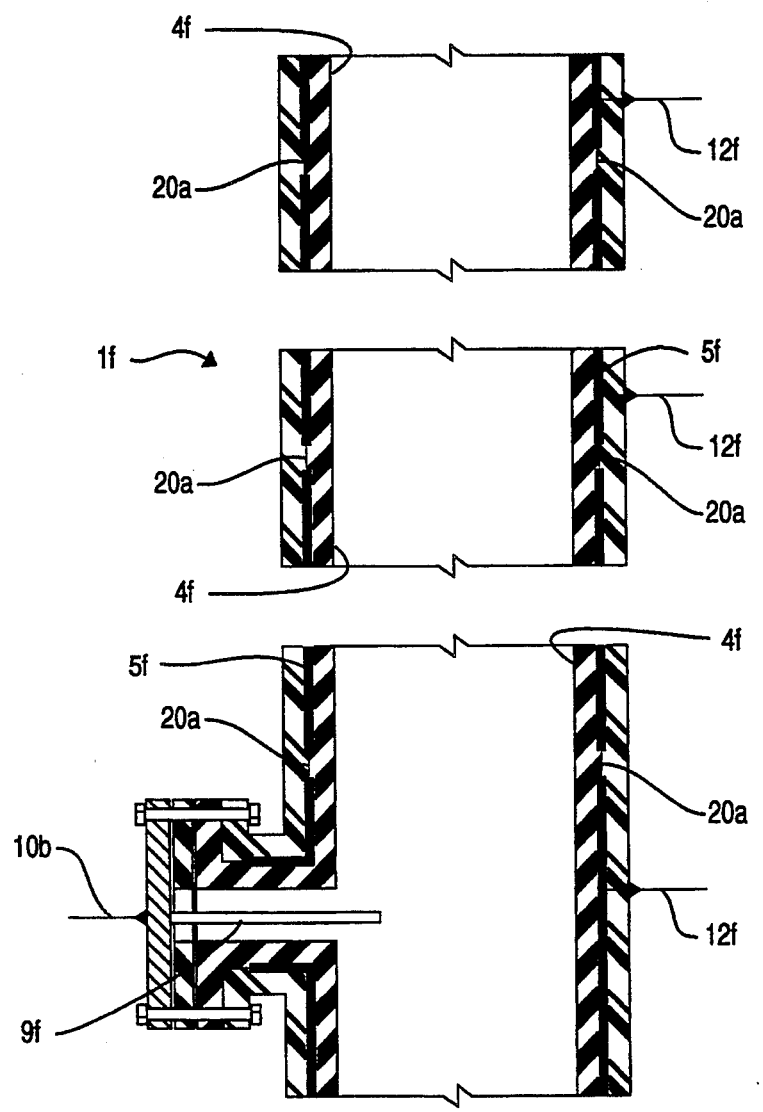

FIG. 7 represents an elongate fluid-containment structure, which, in similar manner to FIG. 6, shows portions of conductive layer 5f with intentional discontinuities 20a that are provided in order to isolate segments of layer 5f for electrical testing. The structure, denoted generally as 1f, has a non-conductive layer 4f on the inside and a middle conductive layer 5f to which there are connection points 12f for connection to an instrument (such as shown in other drawings) which is also connectable to a wire from point 10b on the metal flange cover plate and to which is connected probe 9f for insertion into fluid contained in the structure.

Figure 8:
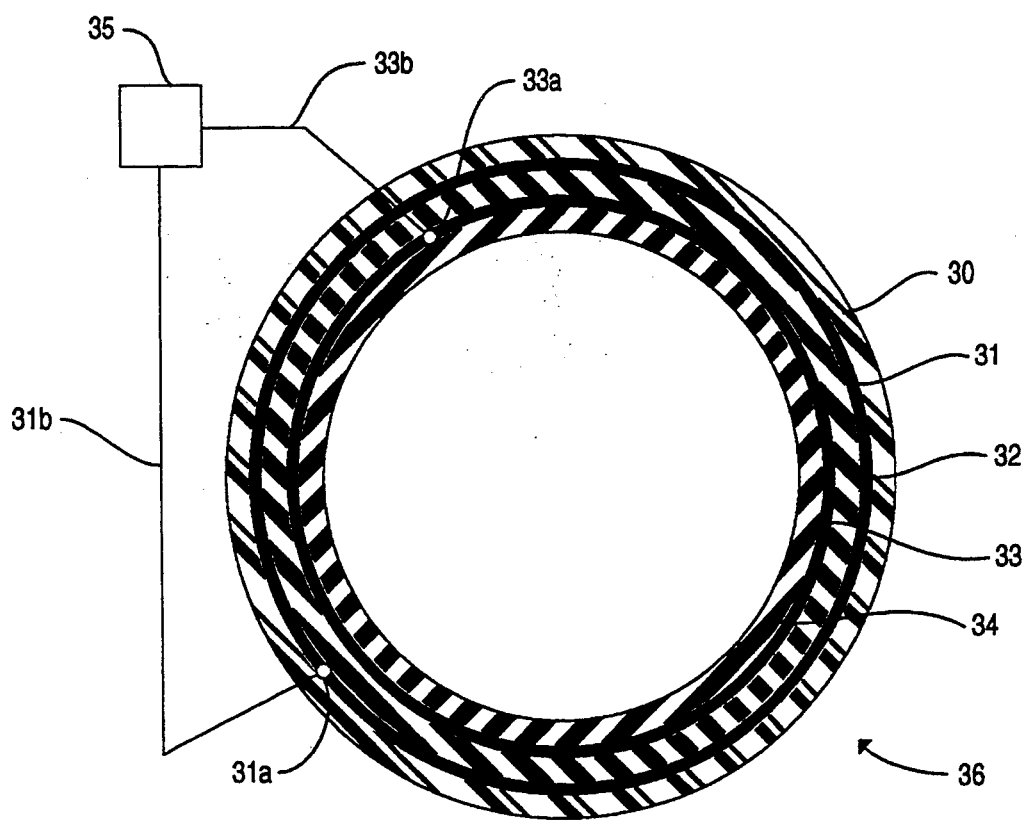

FIG. 8 is provided to demonstrate a fluid-containment having more than one conductive layer embedded co-extensively between non-conductive structural layers. The container, indicated generally as 36, has an outer non-conductive layer 30, surrounding conductive layer 31, which surrounds non-conductive layer 32, which surrounds conductive layer 33, which surrounds inner non-conductive layer 34. Here circuitry is established from a connection point 31a on conductive layer 31 through wire 31b to instrument 35 to which is also connected wire 33b which at site 33a is connected to conductive layer 33. This container can be used for monitoring intrusion of essentially non-conducting fluids, such as hydrocarbons which contain essentially no conductive additives or ingredients, but may tend to dissolve or swell or otherwise make intrusions into the plastic or FRP. Hydrocarbons such as gasoline, kerosene, heating oil, jet fuel, and the like are among the fluids which one finds in plastic or FRP vessels. Intrusions of such fluids into plastic walls of containers can be detected by the present invention, especially by operating the instrument to measure dielectric constant, power factor, loss factor or capacitance.

Furthermore, the FIG. 8 type of double conductive layer construction can be used for detecting intrusions of gas-borne or vapor-borne materials into the walls of fume handling equipment such as hoods, ducts, valves, blowers, flues and stacks, where deterioration of the fluid containment conduit might otherwise go undetected until major problems occur. Also, this double conductive layer type of construction can be used where the fluid containment equipment might be subject to attack by the environment on the outside of the equipment as well as on the inside of it. Electrical circuitry to an instrument can be used to determine changes in resistance of the layers monitored in the circuitry due to deterioration caused by the aggressive substances.

Considering that this invention pertains to changes in the electrical properties of non-conductive materials, then changes in resistance are preferably measured in megohms.

Taking readings with a megohmeter should involve a continuity check of the conductors in the circuitry such as:

I. Continuity check of conductors:
A. Testing the conductive liquid (CL):
1. The conductive liquid, with the container essentially full, shall have two or more separate electrical conductor connections such as:
   a. A connection to a probe that has been inserted through an opening of the container, such as a flanged nozzle;
   b. A connection to the outside of the protective covering of an instrument (i.e. temperature, level, pH) that is inserted into the conductive liquid;
   c. A connection to a metallic cover of a blind flange.
2. The electrical continuity of the system (including the liquid) is checked by reading the ohms resistance between one conductor and each of the other conductors one at a time. Since the resistance, if there is circuit continuity, will be only a few ohms or a few thousand ohms at most; on a multimegohm scale this will be read as zero and means it is all right to use either of the conductors for the corrosion resistant materials, quality test.

B. Testing the electrical conductive layer (ECL):
1. Each electrically conductive layer segment shall have two or more separate electrical connections to separate conductors.
2. The electrical continuity of each conductive layer segment system is checked by reading the ohms resistance between one conductor and each of the other conductors one at a time. Since the resistance, if there is circuit continuity, will be only a few hundred ohms at most, on a multimegohm scale, this will be read as zero and means that any continuity "OK checked" conductor can be used for quality tests of the corrosion resistant material.

II. Inert material service life prediction or damage detection:

A. Single conductive layer (ECL):
1. A CL conductor and an ECL conductor have a voltage of 1000 volts DC applied across them by connecting them to the opposite poles of a megohmeter. The resistance in megohms is read and recorded for that conductor pair as a control base line.
2. Each CL conductor is tested against each ECL conductor and read and recorded by the pairs for a base line for each pair.

B. Multiple conductive layer segments:
1. A CL conductor and an ECL conductor from one segment have a voltage of 1000 volts* DC applied across them by connecting them to opposite poles of the megohmeter. The resistance in megohms is read and recorded for that conductor pair as a control base line. (*voltage can be from less than 1 volt to about 5000 or so volts, depending on which electrical property one wishes to measure; 500 to 1000 volts is generally suitable for measuring megohms in the present invention, though different voltages may be needed in measuring other electrical properties such as amperage, capacitance, power factor, dielectric constant, loss factor, or in scanning for voids using spark generators)
2. Each CL conductor is tested against each ECL conductor in that segment and read and recorded by pairs for a base line for each pair.
3. The tests in 1 and 2 are repeated for each conductive layer segment.
4. One conductor from each ECL segment is joined with one conductor from each of the other ECL segments, and they are connected to one pole of the megohmeter with one CL conductor connected to the other pole of the megohmeter. The megohms resistance is read and recorded.

C. Life prediction or damage detection:
1. When readings are taken after various increments of service time, the megohm values can be plotted vs. time to assist in predicting service life. A sharp drop in resistance would indicate damage caused by an excess mechanical load or severe chemical action (such as cracking).
2. With a significant drop in resistance in a multiple conductive layer hook-up the conductor leads are separated, and each segment is tested separately to find the segment or segments exhibiting change(s) of electrical properties.

Whereas the above description relates to using a megohmeter in making the measurements, practitioners of these relevant arts will be able to employ instrumentation in a manner required for measuring other electrical properties such as amperage, capacitance, power factor, dielectric constant, or loss factor.

Furthermore, the electrical tests can be programmed, through appropriate attachments with computer devices, and used in computer-controlled systems which can also regulate the frequency of making the tests, the frequency of recording the test results on a tracking chart, and can even signal responses to a severe breach or intrusion of the fluid into the non-conductive layer in which is it contained. The response can be audible and/or visible to catch the attention of an operator on duty, or can even be used to automatically activate other equipment for responding to, or mitigating a severe breach or intrusion of the fluid into the non-conductive containment layer, such as when broken or penetrated by an object or force sever enough to cause damage to the containment layer or even to the entire vessel wall. Computer controlled valves, pumps, or other equipment may be used in reducing the effects of an intrusion into, or a breach of, the non-conductive containment layer by the fluid contained therein.

In fume handling equipment (such as hoods, ducts, fans, scrubber, stacks, and the like) there is often no continuous electrically conducting phase to complete a circuit with the electrically conductive layer for testing the electrical properties of the electrical insulating corrosion resistant liner. So an electrically conductive layer is applied within the laminate near the inside surface exposed to the fumes. An electrically conductive layer is also applied to surround the conductive corrosion resistant liner. The two conductive layers are then connected, each to opposing poles of an instrument for measuring electrical properties. Readouts can be obtained at intervals or continuously, if desired, to help determine the remaining expected useful service life of the duct. The properties measured may be, for example, resistance, dielectric constant, power factor, or loss factor.

The following examples are for purposes of relating certain embodiments, but the invention is not limited to the particular embodiments shown. Other practitioners of these arts, upon learning of this invention, may be expected to envision other embodiments without departing from the scope and spirit of the invention proscribed by the attached claims.

EXAMPLE 1

A test vessel having a multi-layered laminated wall structure of non-conductive FRP containing an inner layer of conductive material embedded within, and co-extensive with, the wall structure, and having conductor wires extending from the conductive material for attachment to an instrument for measuring megaohms is prepared using the following materials: surfacing veil of polyester recommended for FRP structures FRP reinforced with layers of chopped & woven fiberglass a thin layer of permeable conductive carbon veil FRP reinforced with layers of chopped & woven fiberglass The structure is such that the layers are permeated by the resin while it is still fluid and not yet cured to solid state. The curing of the resin produces solid, non-porous structure in which the resin is, essentially, a continuous phase and the veils and fiberglass are dispersed phases. The structure is essentially similar to that shown in FIG. 5, except that it is shaped like an open top vessel and has no opening at the bottom. The surface veil of polyester is the fluid containment layer.

The continuity of the conductive veil and the conductors attached to the veil in two spaced apart locations is tested by attaching the protruding conductors to wires extending from opposite poles of the instrument and impressing 1000 volts DC through the circuitry and finding that the conductive layer and the conductors exhibit very low megohms resistance, thus there is very good conductivity through the circuitry. At that point, the instrument can be "zeroed" to "cancel-out" the very slight resistance in the circuitry. Then by moving one of the instrument wires to a conductive probe (copper strip) inserted through the top of the vessel to be in contact with the weak aqueous conductive solution in the vessel (not full to allow further testing as described below), with the other instrument wire still connected to the conductive layer, a very high resistance is registered across the non-conductive containment layer which is in contact with the fluid. On a megaohm scale, the measurement on the instrument dial indicates an infinite amount of resistance.

For illustration purposes, the inventive concept is tested by carefully drilling or scraping small, shallow dents into the non-conductive containment layer at various heights above the level of the fluid, each higher dent coming closer to the conductive layer embedded in the wall of the vessel than the dent below it, there is provided a means for discerning the effects of progressive intrusion of fluid into the non-conductive layer. Adding more aqueous solution to the vessel to bring the level up to the first small dent the instrument measures a lower amount of resistance, indicating that enough intrusion into the wall by the fluid has occurred in order to be detectable. Additional amounts of water, reaching progressively higher, deeper dents, produces instrument readings with less and less resistance.

EXAMPLE 2

In a container constructed substantially in accordance with FIG. 1, with the plastic being fiberglass reinforced polyester, and with the encapsulated conductive layer being a thin porous sheet of carbon, an ohmmeter is employed in measuring the electrical properties of the container wall. Each reading of the electrical properties begins with checking the continuity of the conductive veil and the conductors (using 1000 volts DC and adjusting the ohmmeter to zero (using 1000 volts DC) and to adjust the resistance reading to zero microohms to start with zero resistance as a reference point. By lowering the probe wire into the fluid and taking a read-out of the resistance to determine how far from infinite resistance the reading is, then a benchmark is established. Subsequent readings showing lower and lower resistance of the container indicate that intrusion into the wall by the fluid is getting closer and closer to the conductive layer which is encapsulated within the container wall, thus indicating a shortened life of the container.

By determining if excessive wear or deterioration is occurring, steps can be taken to either repair the wall or replace the container if repair cannot be beneficially done in that particular application.

EXAMPLE 3

A multi-layer laminate vessel for containment of a non-conductive fluid is provided which has an inner conductive layer comprising a graphite veil which is impregnated with a resin; this provides the fluid-containment portion of the vessel. A non-conductive FRP layer surrounds the conductive layer and a conductive layer surrounds the non-conductive FRP layer. Electrical conductors extend from the inner layer for connection to an instrument for measuring electrical properties. The conductor attached to the inner layer is insulated from contact with the outer conductive layer where it passes through it. Electrical conductors extend from the outer conductive layer for connection to the instrument for measuring electrical properties.

Intrusion or penetration of contained fluid through the inner conductive layer, which causes loss of integrity of the container wall, is determined by monitoring the dielectric constant, power factor, and loss factor between the conductive layers.

EXAMPLE 4

In a similar manner to Example 3 above, except that the multi-layer laminate vessel which comprises the same type of inner fluid containment conductive layer, surrounded by an FRP layer, a second conductive layer comprising a carbon veil, and a second FRP layer, is tested. Intrusion or penetration of fluid through the inner conductive layer, which causes loss of integrity of the container wall, is determined by monitoring the dielectric constant, power factor, and loss factor between the conductive layers.

What is claimed is:

1. A fluid container having a multi-layered wall construction of which at least one layer is a conductive layer, said container comprising
   an inner layer for containment of fluid, the said inner layer comprising a substantially non-permeable, electrically, non-conductive, substantially inert material,
   co-extensively enveloping said inner layer, and co-extensively in intimate contact therewith, a first layer of conductive material which is separated from contact with fluid in the container by the non-conductive inner layer,
   and having connected to the said first layer of conductive material at least one first conductor extending therefrom, said first conductor being connectable to instrumentation wiring outside the container for measuring electrical properties,
   said container further having at least one probe site provided thereon for application of at least one second conductor for contact with fluid in the container, said second conductor being connectable to the instrumentation to which the first conductor wire is connectable for completing circuitry between fluid and conductive layer for making electrical measurements across the electrically non-conductive inner layer,
   and wherein there is at least one additional non-conductive layer which surrounds the said first conductive layer, and at least one additional conductive layer which surrounds each additional non-conductive layer, each of the additional conductive layers being provided with conductors extending therefrom for connection with an instrument for measuring electrical properties between each conductive layer and at least one wettable probe immersible in fluid in the containment portion of the container.

2. The container of claim 1 wherein the non-conductive substantially inert material is comprised of at least one material selected from the group consisting of ceramic material, refractory material, vitreous material, plastic, rubber, polymer and resin.

3. The container of claim 1 wherein the non-conductive layer material is comprised of at least one material selected from the group consisting of epoxy resin, polyurethane, polyester, vinyl ester resin, polyolefin, polydiolefin, polyhaloolefin, polymer of substituted olefin, polymer of substituted diolefin, polyvinyl halide, polyvinyl chloride, polyvinylidene chloride, polyvinylfluoride, polyvinylidene fluoride, polycarbonate, polyethyleneterephalate, polyacrylonitrile, polymetharcylate, and polyacrylate.

4. The container of claim 1 wherein the non-conductive layer for containment of fluid is FRP.

5. The container of claim 1 having a conductive layer comprised of at least one material selected from the group consisting of porous metal, carbon veil, graphite veil, and conductive plastic.

6. The container of claim 1 wherein at least one conductor used for connection to the instrument is comprised of a member of the group consisting of copper, silver, gold, steel, nickel, aluminum, and platinum.

7. The container of claim 1 wherein the conductive layer is a layer sandwiched between the inner non-conductive layer and a third layer which surrounds the conductive layer, said third layer being a non-conductive layer.

8. The container of claim 1 wherein the conductive layer is a layer sandwiched between the inner non-conductive layer and a third layer which provides structural strength and which surrounds the conductive layer, and which is comprised of a different material than that used for the inner non-conductive layer.

9. The container of claim 1 wherein the fluid containment portion of the container comprises at least part of at least one of the group consisting of a vessel, barge, pipe, conduit, duct, flume, tank, rail car, tank truck, valve and pump, any of which can comprise metal as the principal structural layer.

10. The container of claim 1 wherein the inner layer is for containment of a fluid which is conductive.

11. The container of claim 1 wherein the probe site provided for positioning a conductor into contact with fluid in the container comprises a conductive surface which covers, or protrudes into, a port or nozzle opening which communicates with fluid in the fluid-containment portion of the container,
said conductor being attachable and removable without involving the innermost surface of the containment layer of the multi-layer wall.

12. The container of claim 1 wherein the probe site provided for positioning the probe into contact with fluid in the container comprises one at which the probe can be applied, and from which the probe can be removed, without involving or affecting the innermost surface on the fluid-containment layer of the multi-layer wall.

13. A system for detecting deterioration of a fume duct through which fumes, comprising corrosive material carried as a dispersed phase in a gaseous carrier, are transported, said system comprising providing as the fume duct a multi-layered conduit of appropriate size, shape and length for transporting the fumes, said conduit comprising laminated alternate layers of electrically conductive and non-conductive layers, providing electrical connections between each of the conductive layers to an instrument for measuring electrical properties, and obtaining read-outs indicating deterioration of the said fume duct.

14. A multi-layered container for a non-conductive fluid, said container comprising a conductive, substantially inert inner layer for containment of a non-conductive fluid, said inner layer separating the fluid from a first non-conductive layer which encircles said inner layer and is co-extensively in contact therewith, a third layer which is conductive and which encircles the non-conductive layer and is co-extensively in contact therewith, each of the said conductive layers having electrical conductors extending therefrom for attachment to an instrument for measuring electrical properties.

15. The container of claim 14 wherein the fluid is an organic material.

16. The container of claim 14 wherein the fluid is a hydrocarbon.

17. A multi-layered elongate structure for containing a fluid said structure comprising a non-conductive inner layer for fluid containment, covered by a conductive layer, a plurality of probe sites each for attachment of a conductor for contact with fluid in the structure without being in contact with the said conductive layer, each of said probes providing circuitry with an instrument for measuring electric properties, and a plurality of sites on the conductive layer for attachment of conductors for providing circuitry with an instrument which is in circuitry with conductors in contact with the fluid.

18. The structure of claim 17 wherein the non-conductive layer is a material selected from the group consisting of refractory material, ceramic material, vitreous material, epoxy resin, urethane resin, polyvinyl ester, polyester, polyolefin, polydiolefin, polymer of substituted olefin, polyhaloolefin, polyvinyl chloride, polyvinylidene chloride, polyvinyl fluoride, polyvinylidene fluoride, polycarbonate, polyethyleneterephalate, polymethacrylates, and polyacrylates.

19. The structure of claim 17 wherein the non-conductive layer is reinforced with non-conductive fibrous material.

20. The structure of claim 17 wherein the non-conductive layer is selected from the group consisting of polyepoxy, polyurethane, polyester, and polyvinyl ester, and is reinforced with fiberglass.

21. The structure of claim 17 wherein the conductive layer is caused to be conductive by incorporating therein a reticulated conductive form of a material selected from the group comprising a veil, cloth, mesh, screen carbon, graphite, and metal.

22. The structure of claim 17 wherein the conductor is a wire selected from the group comprising copper, silver, gold, steel, nickel, aluminum and platinum.

23. The method of claim 17 wherein the instrument is an ohmmeter and the zeroing is done by adjusting the read-out of the instrument to read as zero when a dead short is created by contacting the probe wire with the pole to which the first wire is connected, then the probe wire is inserted into the fluid in the container to obtain a reading to compare with the zeroed reading.

24. The structure of claim 17 wherein the conductive layer is covered by a non-conductive layer.

25. The structure of claim 17 wherein there are preselected sites of non-conductivity provided in the conductive layer to create zones whereby different probes are provided for attachment to different portions of the conductive layer for measuring individual zones in the structure.

26. The structure of claim 17 wherein the elongate structure is of the group comprising pipelines, conduits, fume ducts, tanks and towers.

27. The method for detecting porosity in the corrosion resistant, non-conductive plastic liner of a non-conductive FRP container for corrosive fluids, said container having a conductive veil laminated between the said liner and FRP,
 wherein the FRP provides essentially all the structural strength of the wall of said container, said process comprising
 operating the discharge probe of a high voltage spark generator over the surface of the FRP container, noting any places where a visibly strong spark finds a route through the plastic to the conductive veil, thus indicating areas of deleterious porosity in the non-conductive liner which indicates a need for taking corrective action.

28. A multi-layered elongate structure for containing a fluid, said structure comprising a first non-conductive inner layer for fluid containment, covered by a conductive layer,
 said conductive layer being covered by a second non-conductive layer,
 said conductive layer having preselected sites of non-conductivity which provides a plurality of zones in the structure for individual measurement of electrical properties in the zones,
 a plurality of probe sites each for attachment of a conductor for contact with fluid in the structure without being in contact with the said conductive layer, each of said probes providing circuitry with an instrument for measuring electric properties in a given zone,
 and a plurality of sites on the conductive layer for attachment of conductors for providing circuitry with an instrument which is in circuitry with conductors in contact with the fluid.

* * * * *